US 6,617,070 B1

United States Patent
Morrissey et al.

(10) Patent No.: US 6,617,070 B1
(45) Date of Patent: Sep. 9, 2003

(54) METHODS OF DETECTING THE ONSET OF COLLOID FORMATION IN PARTICULAR SULFUR PRECIPITATION

(75) Inventors: Patrick John Morrissey, Uxbridge (GB); Graham Edward Cooley, Oxon (GB)

(73) Assignee: Regenesys Technologies Limited, Swindon (GB)

( * ) Notice: Subject to any disclaimer, the term of this patent is extended or adjusted under 35 U.S.C. 154(b) by 0 days.

(21) Appl. No.: 09/980,313
(22) PCT Filed: Jun. 7, 2000
(86) PCT No.: PCT/GB00/02206
§ 371 (c)(1),
(2), (4) Date: Apr. 11, 2002
(87) PCT Pub. No.: WO00/74839
PCT Pub. Date: Dec. 14, 2000

(30) Foreign Application Priority Data

Jun. 7, 1999 (GB) .............................................. 9913185

(51) Int. Cl.[7] .................................................. H01M 4/36
(52) U.S. Cl. ........................ 429/105; 429/106; 429/107
(58) Field of Search ................................ 429/105, 106, 429/107

(56) References Cited

U.S. PATENT DOCUMENTS 5,612,148 A * 3/1997 Zito ............................ 248/582

FOREIGN PATENT DOCUMENTS

WO       WO 9429694    * 12/1994   .......... G01N/15/02

* cited by examiner

Primary Examiner—Carol Chaney
Assistant Examiner—Dah-Wei D. Yuan
(74) Attorney, Agent, or Firm—Antonelli, Terry, Stout & Kraus, LLP

(57) ABSTRACT

A method suitable for detecting the onset of colloid formation within a solution whose composition is in a state of change, which method makes use of the technique of acoustophoresis and which comprises the step of either (I) applying an oscillating electric field to the solution and monitoring the amplitude of the resultant acoustic signal, the onset of colloid formation being detected by a change in the amplitude of the resultant acoustic signal, or (ii) applying an oscillating acoustic signal to the solution and monitoring the resultant oscillating electric field, the onset of colloid formation being detected by a change in the amplitude of the resultant oscillating electric field, or (iii) applying an oscillating electric field to the solution and monitoring the resultant oscillating electric field, the onset of colloid formation being detected by a change in the amplitude of the resultant oscillating electric field.

5 Claims, 3 Drawing Sheets

Variation in ESA signal with added sulphur in 1.61 M Na₂S

Variation in ESA signal with added sulphur in 0.76 M Na₂S

METHODS OF DETECTING THE ONSET OF COLLOID FORMATION IN PARTICULAR SULFUR PRECIPITATION

The present invention relates to a method for detecting the formation o colloidal species in solutions and in particular to a method for detecting the formation of sulfur-containing colloidal species within an aqueous solution which comprises polysulfide ions, and which may also comprise sulfide ions and/or hydroxide ions and/or sulfur.

U.S. Pat. No. 4,485,154 discloses an electrically rechargeable anionically active reduction-oxidation electricity storage/supply system and process using a sulfide/polysulfide anolyte reaction in one half of the cell and a halide/halogen catholyte reaction in the other half of the cell. The catholyte reaction is:

$$Hal_2 + 2e^- = 2Hal^-$$

On discharging the system the reaction moves from left to right and on charging the system the reaction moves from right to left. The catholyte reaction is:

$$S_2^- = S + 2e^-$$

On discharging the system the reaction moves from left to right and on charging the system the reaction moves from right to left.

When the system is fully charged the sulfur in the anolyte is present as sulfide ions. As the system discharges elemental sulfur is produced which then dissolves in the anolyte solution by combination with sulfide ions to form polysulfide species such as $S_2^{2-}$, $S_3^{2-}$, $S_4^{2-}$ and $S_5^{2-}$. However, at a certain point in the discharge cycle there will no longer be sufficient sulfide ions present to solubilize the elemental sulfur as a polysulfide and consequently the elemental sulfur precipitates out of solution. In a solution of $Na_2S$ this would be expected to occur when the ratio of S/Na exceeds approximately 2.5. When the ratio is equal to 2.5 the elemental sulphur is solubilized as $Na_2S_5$, however, when the ratio exceeds 2.5 the elemental sulphur can no longer be solubilized as a polysulfide and consequently precipitates but of solution. It should be, noted however that the equilibrium between sulfur and aqueous polysulfides is strongly dependent upon the alkalinity of the solution. Longer polysulfide chains may be formed in alkaline solutions thus delaying the onset of precipitation until a higher ratio of S/Na is reached.

The formation of a precipitate of sulfur within the anolyte is undesirable because it may be deposited on the electrode reducing its conductivity and reducing the overall performance of the system. Thus it would be desirable to provide a method for detecting the onset of precipitation of sulfur from the anolyte so that the system may be switched over to the charge cycle before sulfur precipitates in the anolyte.

It is known that sulfur forms a colloidal species immediately prior to forming a precipitate. The nature of the sulfur colloidal species is discussed by R. Steudel, T. Gobel and G. Holdt in Z. Naturforsh. 43b, 203–218 (1987) and Z. Naturforsh. 44b, 526–530 (1989). The sulfur colloid is known to have a charged "micelle-like" structure. If the formation of the colloidal species could be detected then this would provide a warning signal that the precipitation of sulfur is imminent and that the system should be switched over to the charge cycle to prevent precipitation occurring.

It is also known that charged particles, such as the charged "micelle-like" structures of colloidal sulfur, can be detected by the technique of acoustophoresis. The principle of the technique is as follows. If an electric field is applied across a charged colloidal particle it will move in that field. In an oscillating electric field the motion of the particle will be proportional to the magnitude and frequency of the field. If a high frequency field is applied, and the particles respond, then high frequency motion will result. In acoustophoresis is the applied frequency is typically $10^6$ Hz. Particle motion at this frequency generates a mechanical pressure wave with a magnitude characteristic of the mobility of the particle, its concentration and the density of the overall composition containing the particle. This is an acoustic wave travelling at the velocity of sound in the medium and the amplitude of the signal is called the Electrokinetic Sonic Amplitude (ESA). The ESA signal can be monitored as the overall composition changes, a sharp change in the ESA signal may be indicative of the creation of a new charged species within the composition. A review of electroacoustic phenomena has been made by Babchin et al.(Babchin, A. J.; Chow, R. S.; Sawatzky, R. P.; "Electrokinetic Measurements by Electroacoustical Methods", Advances in Colloid and Interface Science, 1989, Vol. 30, No. 1–2, pp. 111–151).

Accordingly, the present invention provides a method of detecting the onset of colloid formation within a solution whose composition is in a state of change, which method comprises the steps of either (i) applying an oscillating electric field to the solution and monitoring the amplitude of the resultant acoustic signal, the onset of colloid formation being detected by a change in the amplitude of the resultant acoustic signal, or (ii) applying an oscillating acoustic signal to the solution and monitoring the resultant oscillating electric field, the onset of colloid formation being detected by a change in the amplitude of the resultant oscillating electric field, or (iii) applying an oscillating electric field to the solution and monitoring the resultant oscillating electric field, the onset of colloid formation being detected by a change in the amplitude of the resultant oscillating electric field.

Preferably the method uses step (i) of the three options listed above.

The present invention will be further described with reference to the figures in which.

Figure 1:
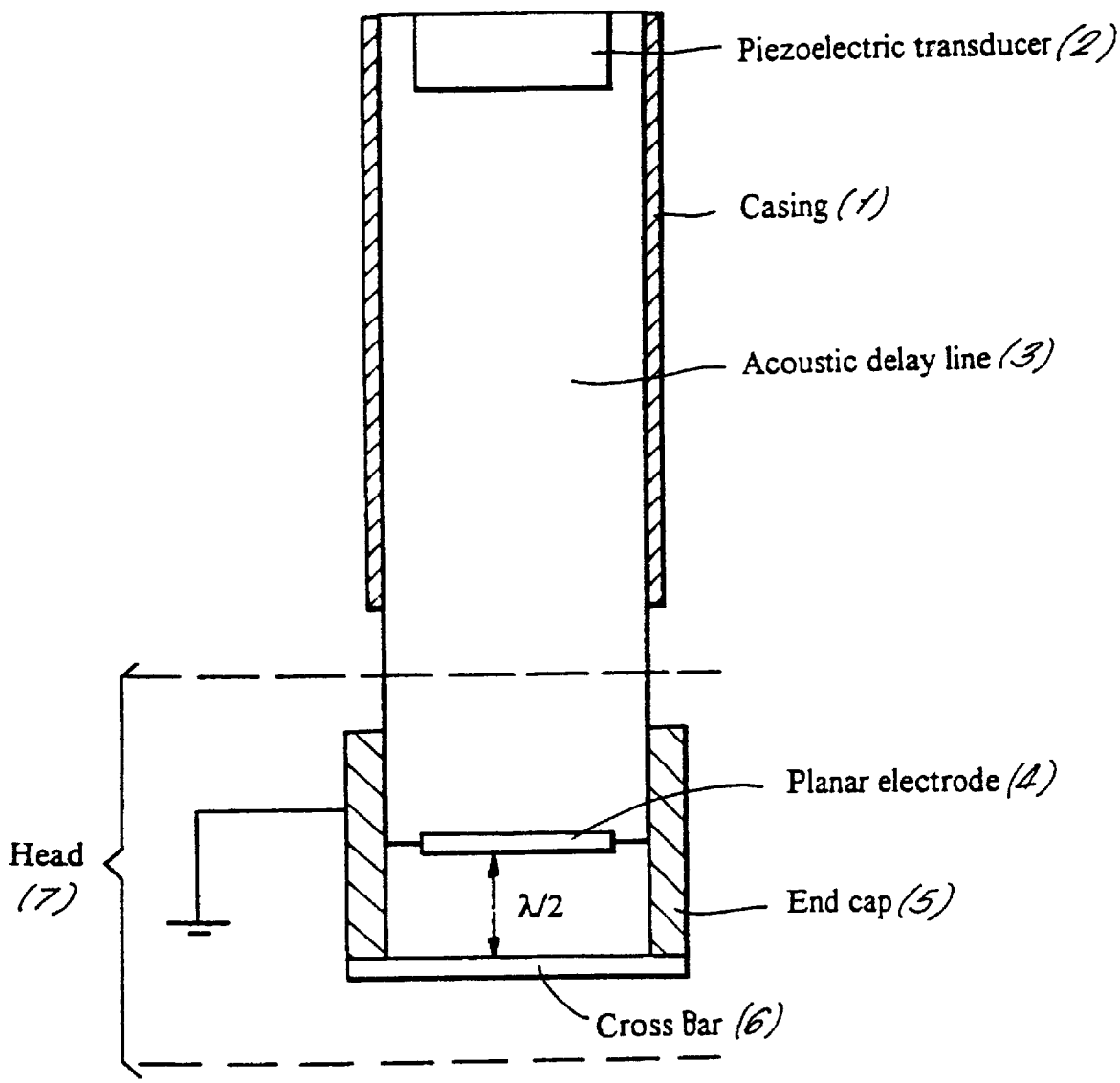
FIG. 1 shows a schematic representation of a probe suitable for use in the present invention.

Measurements of the ESA signal can be carried out using, for example, a Matec ESA Probe. FIG. 1 shows a schematic representation of a Matec ESA Probe. The probe consists of a cylindrical tube casing (1) with two coaxial fittings at one end which allow transmission and reception from the transducer (2). The transducer is a piezoelectric device mounted on one end of the probe. This is attached to one end of a delay line (3) and on the other end is a solid gold laminated electrode (4). This electrode is electrically isolated from a gold cap (5) with a cross bar (6) which forms the other part of the electrode assembly. The cross bar is positioned in a plane parallel to the gold electrode. The gap ($\lambda/2$) between the cap and the main body of the probe gives an electrode spacing of one half the acoustic wavelength in the system. The acoustic delay line serves the simple purpose of separating in time the energising radiofrequency (RF) pulse from the ESA signal. The head (7) of the probe is immersed in the solution to be monitored and measurements of the ESA are made. This requires two steps. Firstly, the probe needs to be calibrated, this is done by sweeping through a range of frequencies and finding the condition for the maximum in the amplitude of the received signal. The optimum frequency will vary depending on the nature of the species being detected. Secondly, after establishing the optimum frequency for the measurements the ESA measurements can be made at this frequency. Preferably the frequency is in the range of from 0.8 to 1.2 MHz. More preferably the frequency is approximately 1.0 MHz.

The ESA can be thought of as an apparent elastic modulus that arises from a given applied electric field. It has the dimension of Pascal per volt meter, i.e. $Pa.m.V^{-1}$. For typical colloidal systems, the ESA obtained is in the range of $mPa.m.V^{-1}$ Although the technique commonly used involves applying an oscillating electric field to the materials and monitoring the resultant acoustic signal it will be appreciated by those skilled in the art that the technique may also be carried out either by applying an acoustic signal and monitoring the amplitude of the resultant oscillating electric field, or by applying an oscillating electric field and monitoring the amplitude of the resultant oscillating electric field.

In a preferred embodiment of the present invention the method is employed in the detection of the formation of colloids comprising sulfur within a solution comprising polysulfide ions. The solution may also, comprise sulfide ions and/or hydroxide ions and/or halide ions and/or sulfur. More preferably the solution comprises one or more alkali metal cations as the counter ions to the anions listed above. Most preferably the alkali metal is sodium.

The method of the present invention may advantageously be employed in an electrochemical process for energy storage and/or power delivery, which process comprises the steps of:

(i) maintaining and circulating electrolyte flows in a fully liquid system in which the active constituents are fully soluble in a single cell or in an array of repeating cell structures, each cell with a chamber (,+ve chamber) containing an inert +ve electrode and a chamber (−ve chamber) containing an inert −ve electrode, the chambers being separated from one another by an ion exchange membrane, the electrolyte circulating in the −ve chamber of each cell during power delivery containing a sulphide, and the electrolyte circulating in the +ve chamber during power delivery containing bromine as an oxidising agent, (ii) restoring or replenishing the electrolytes in the +ve and −ve chambers by circulating the electrolyte from each chamber to storage means comprising a volume of electrolyte greater than the cell volume for extended delivery of power over a longer discharge cycle than the cell volume alone would permit, and (iii) monitoring the electrolyte stream containing sulfide as a reducing agent according to the method described above in order to detect the onset of colloid formation within the electrolyte stream.

The present invention will be further described by way of the following examples which are intended to be illustrative of the invention but are not intended to be limiting on the scope of the invention.

EXAMPLE 1

A saturated solution (2.3M) of sodium sulphide in water was prepared. Sulphur in the form of pastilles was then added periodically to the solution of $Na_2S$ and the ESA signal (units=$mPa.m.V^{-1}$) was measured after each addition using a Matec ESA probe until the ratio of S/Na in the mixture was approximately 2.5. The results are shown in the table below:

| S:Na ratio | Mass fraction of sulphur, $f_s$ | ESA signal, $mPa.m.V^{-1}$ |
|---|---|---|
| 0.50000 | 0.00000 | 0.05350 |
| 0.58004 | 0.00988 | 0.06700 |
| 1.03635 | 0.06270 | 0.07000 |
| 1.42193 | 0.10312 | 0.08600 |
| 1.68744 | 0.12899 | 0.09125 |
| 2.00069 | 0.15766 | 0.09325 |
| 2.19880 | 0.17483 | 0.10700 |
| 2.28364 | 0.18197 | 0.11350 |
| 2.42700 | 0.19376 | 0.12475 |

Figure 2A:
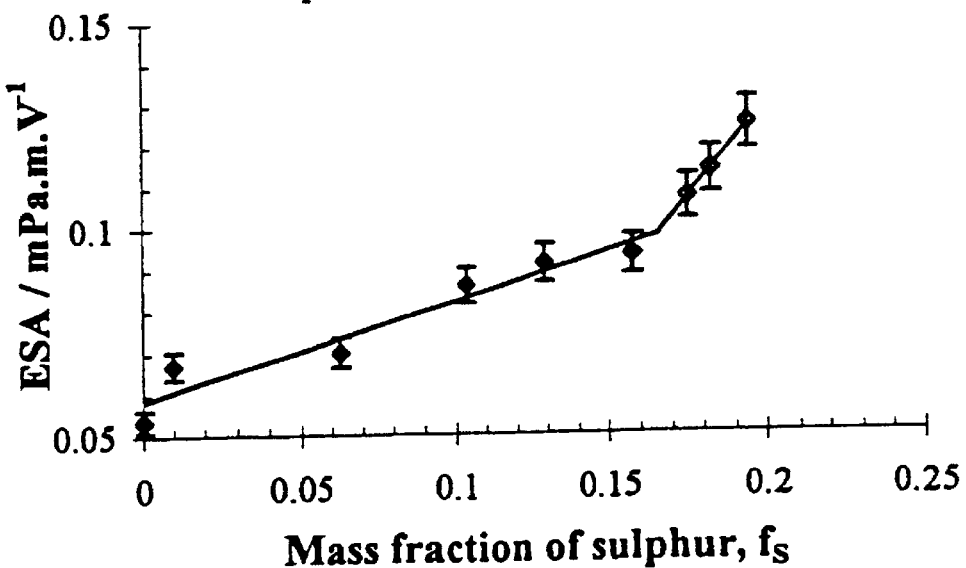
FIGS. 2A and 2B show the variation in ESA signal with addition of sulphur to a saturated solution of $Na_2S$.
Figure 2B:
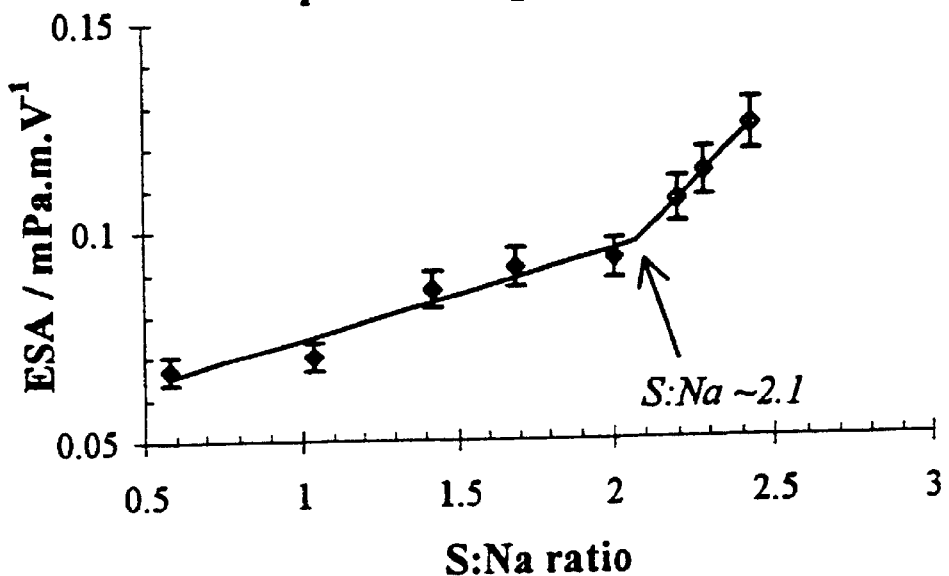

Plots of the ESA signal against the mass fraction of sulphur and against the ratio of S/Na are shown in FIGS. 2A and 2B respectively. A sharp increase in the slope of the FIG. 2B plot was found to occur at a ratio of S/Na of approximately 2 indicating the onset of colloid formation at this point.

EXAMPLE 2

Two non-saturated solutions (1.61M and 0.76M) of sodium sulphide in water were prepared. Sulphur in the form of pastilles was then added periodically to the solutions of $Na_2S$ and the ESA signal (units=$mPa.m.V^{-1}$) was measured after each addition using a Matec ESA probe until the ratio of S/Na in the mixture was approximately 2.5. The results are shown in the tables below:

| 1.61 M solution | |
|---|---|
| S:Na ratio | ESA signal, $mPa.m.V^{-1}$ |
| 0.862500 | 0.14650 |
| 1.218040 | 0.15950 |
| 1.574297 | 0.16800 |
| 1.767007 | 0.14433 |
| 1.976514 | 0.16250 |
| 2.148604 | 0.16850 |
| 2.433799 | 0.18850 |
| 2.500219 | 0.19100 |

| 0.76 M solution | |
|---|---|
| S:Na ratio | ESA signal, $mPa.m.V^{-1}$ |
| 0.86115 | 0.1465 |
| 1.26380 | 0.1465 |
| 1.57880 | 0.1430 |
| 1.80470 | 0.1410 |
| 1.96170 | 0.1420 |
| 2.14230 | 0.1490 |
| 2.37920 | 0.1710 |
| 2.55360 | 0.1970 |

Figure 3A:
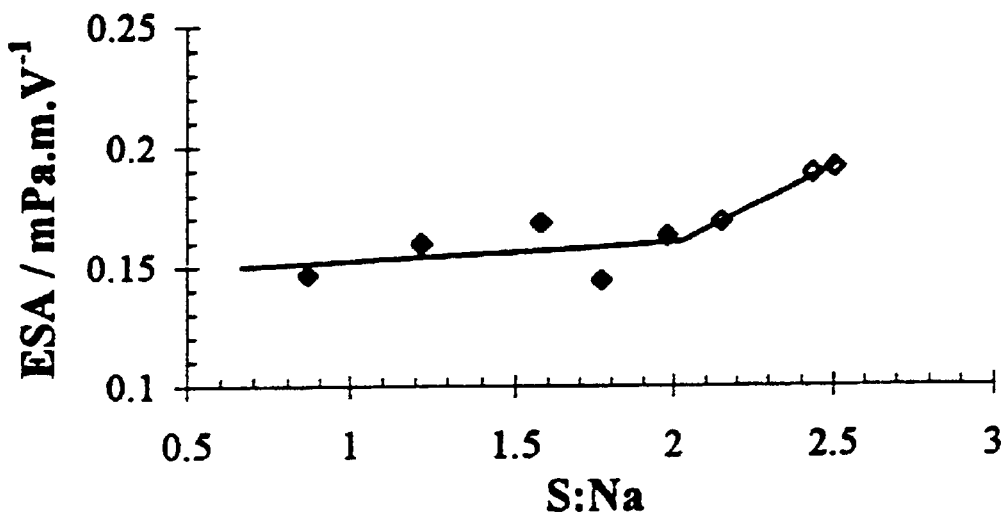
FIGS. 3A and 3B show the variation in ESA signal with addition of sulphur to solutions of 1.61M and 0.76M $Na_2S$ respectively.
Figure 3B:
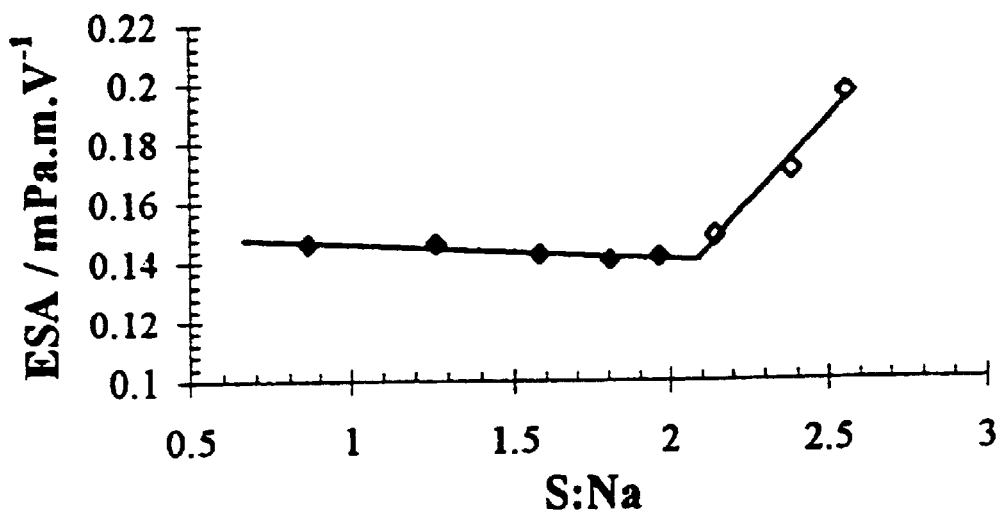

Plots of the ESA signal against the ratio of S/Na for the 1.61M and 0.76M solutions are shown in FIGS. 3A and 3B respectively. Sharp increases in the slopes of the plots were found to occur at a ratio of S/Na of approximately 2 indicating the onset of colloid formation at this point.

What is claimed is:

1. An electrochemical process for energy storage and/or power delivery comprising the steps of:

(i) maintaining and circulating electrolyte flows in a fully liquid system in which the active constituents are fully soluble in a single cell or in an array of repeating cell structures, each cell with a chamber (+ve chamber) containing an inert +ve electrode and a chamber (−ve chamber) containing an inert −ve electrode, the chambers being separated from one another by an ion exchange membrane, the electrolyte circulating in the −ve chamber of each cell during power delivery containing a sulphide, and the electrolyte circulating in the +ve chamber during power delivery containing bromine as an oxidising agent, (ii) restoring or replenishing the electrolytes in the +ve and −ve chambers by circulating the electrolyte from each chamber to storage means comprising a volume of electrolyte greater than the cell volume for extended delivery of power over a longer discharge cycle than the cell volume alone would permit, and (iii) monitoring the electrolyte stream containing sulfide as a reducing agent in order to detect the onset of colloid formation within said electrolyte stream by a method which comprises applying an oscillating electric field to the solution and monitoring the amplitude of the resultant acoustic signal, the onset of colloid formation being detected by a sharp change in the amplitude of the resultant acoustic signal.

2. A method as claimed in claim 1 wherein the frequency of the applied oscillating electric field is in the range of from 0.8 to 1.2 MHz.

3. A method as claimed in claim 1 wherein the frequency of the applied oscillating electric field is approximately 1.0 MHz.

4. A method as claimed in claim 1 wherein the solution which is in a state of change comprises polysulfide ions and the colloidal species, the onset of whose formation is to be detected, comprise sulfur.

5. A process as claimed in claim 4 wherein the alkali metal is sodium.

* * * * *